US007544508B2

(12) United States Patent   (10) Patent No.: US 7,544,508 B2
Cinquin et al.   (45) Date of Patent: Jun. 9, 2009

(54) OSMOTIC ACTUATOR AND ENGINE

(75) Inventors: Philippe Cinquin, Saint Nazaire les Eymes (FR); Olivier Cinquin, Saint Nazaire les Eymes (FR)

(73) Assignee: Universite Joseph Fourier, Grenoble Cedex (FR)

( * ) Notice: Subject to any disclaimer, the term of this patent is extended or adjusted under 35 U.S.C. 154(b) by 685 days.

(21) Appl. No.: 10/505,860

(22) PCT Filed: Feb. 24, 2003

(86) PCT No.: PCT/FR03/00592

§ 371 (c)(1),
(2), (4) Date: Mar. 11, 2005

(87) PCT Pub. No.: WO03/072941

PCT Pub. Date: Sep. 4, 2003

(65) Prior Publication Data

US 2005/0158841 A1   Jul. 21, 2005

(30) Foreign Application Priority Data

Feb. 28, 2002 (FR) .................................. 02 02558

(51) Int. Cl.
*C12M 1/00* (2006.01)
(52) U.S. Cl. .............. 435/289.1; 435/283.1; 435/287.4; 435/252.3
(58) Field of Classification Search ............ 210/321.64, 210/601, 621, 321.71, 624; 435/7.37, 252.4, 435/287.4; 438/1; 530/414; 604/315; 60/205, 60/222, 503, 518, 522, 530
See application file for complete search history.

(56) References Cited

U.S. PATENT DOCUMENTS

| 3,587,227 | A | * | 6/1971 | Weingarten et al. ........... 60/326 |
| 3,894,538 | A | | 7/1975 | Richter |
| 4,181,604 | A | * | 1/1980 | Onishi et al. ................ 210/615 |
| 4,838,862 | A | | 6/1989 | Baker et al. |
| 4,898,582 | A | | 2/1990 | Faste |
| 5,032,271 | A | * | 7/1991 | Urry .......................... 210/350 |
| 5,256,279 | A | * | 10/1993 | Voznick et al. ................ 210/86 |
| 5,279,608 | A | | 1/1994 | Cherif Cheikh |
| 6,436,091 | B1 | * | 8/2002 | Harper et al. ............ 604/892.1 |
| 6,509,164 | B1 | * | 1/2003 | Guirguis ..................... 435/7.2 |

OTHER PUBLICATIONS

International Search Report dated Aug. 21, 2003 for related PCT Application No. PCT/FR 03/00592.

* cited by examiner

*Primary Examiner*—William H Beisner
*Assistant Examiner*—Michael Hobbs
(74) *Attorney, Agent, or Firm*—Howard IP Law Group, PC

(57) ABSTRACT

An actuator for arrangement in contact with a biological solvent includes a housing with a wall which is permeable to the solvent and not permeable to a first solute and which contains micro-organisms for transforming a second solute into the first solute. The actuator further includes a deformable chamber connected to the housing which can increase in volume due to the solvent entering the housing by osmosis. An engine may make use of the actuator.

18 Claims, 3 Drawing Sheets

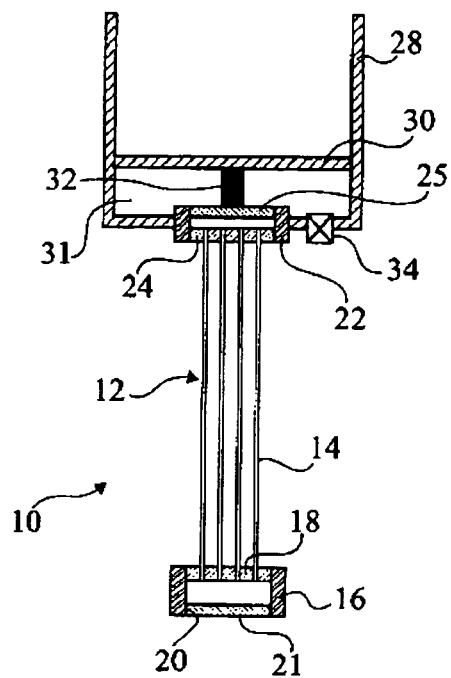 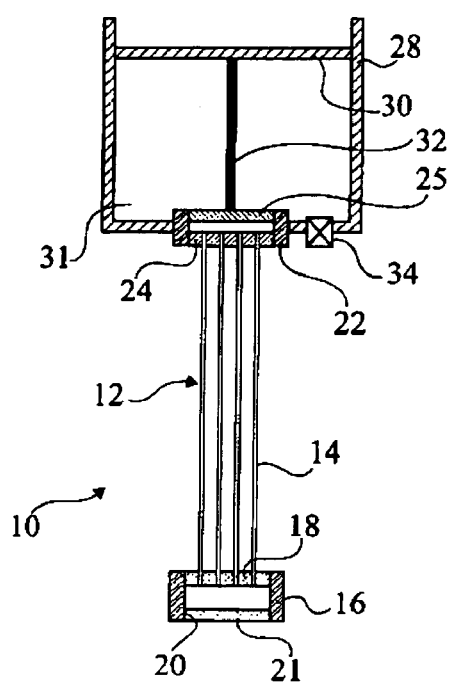
Fig 1A  Fig 1B
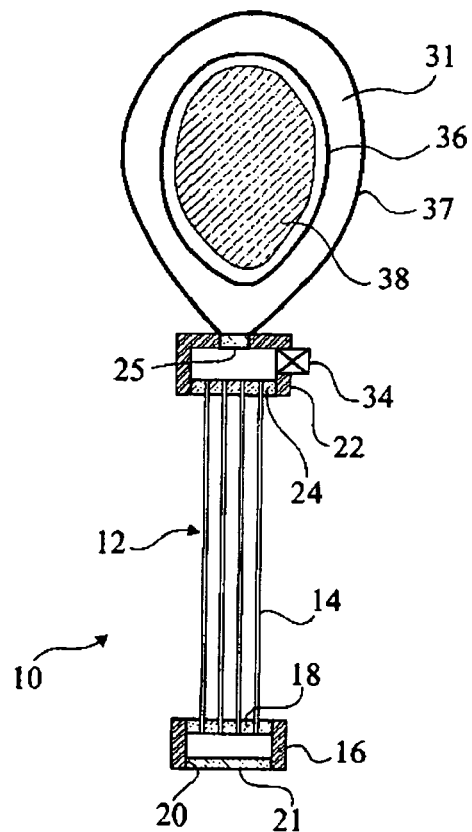 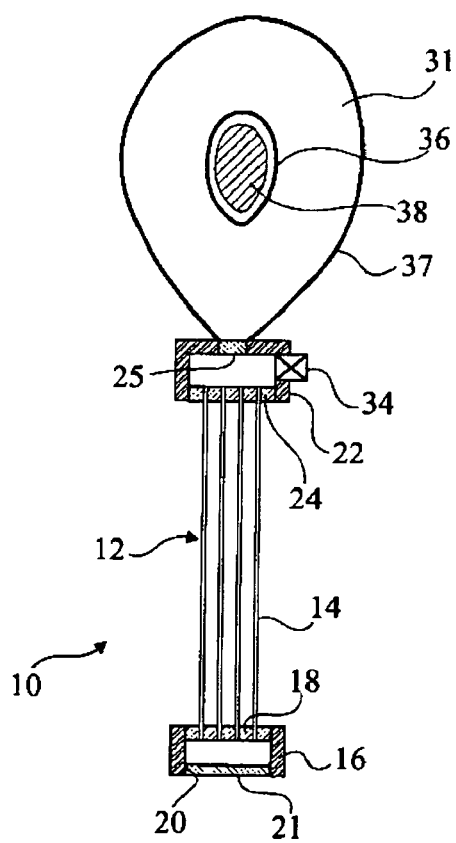
Fig 2A  Fig 2B

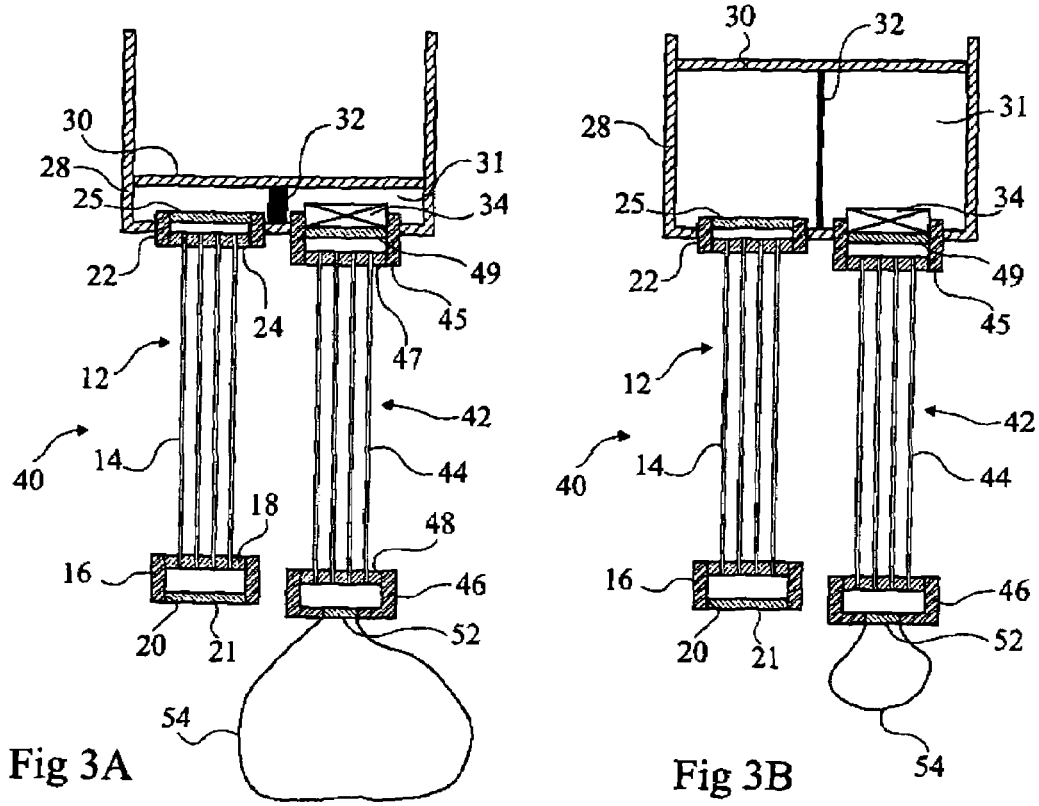
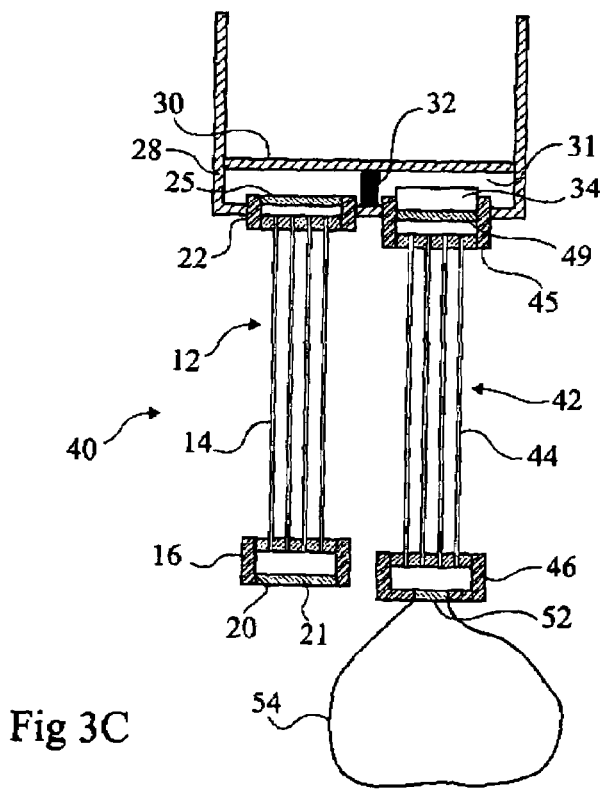
Fig 3A
Fig 3B
Fig 3C

OSMOTIC ACTUATOR AND ENGINE

This application is the national stage application under 35 U.S.C. § 371 of the International Application No. PCT/FR03/00592 and claims the benefit of French Application No. 02/02558, filed Feb. 28, 2002 and Int'l Application No. PCT/FR03/00592, filed Feb. 4, 2003, the entire disclosures of which are incorporated herein by reference in their entireties.

BACKGROUND OF THE INVENTION

The present invention relates to devices usable as an actuator or a motor which are simple to form, which use low-cost fuel, and which emit little or no waste.

Further, the present invention relates to devices usable as an actuator or a motor capable of operating inside of a biological medium such as the human body or an animal body.

Such actuators or such motors find applications in the medical field, for example, to palliate the deficiency of a natural muscle. The muscles that can be replaced or assisted, temporarily or definitively, are, for example, the heart muscle, the respiratory muscles, the sphincter, and non-striated or striated muscles, in particular, skeletal muscles.

Such actuators and such motors also find applications in fields other than the medical field. In particular, such a motor may be used in all the fields where a small waste generation is an important factor in the motor selection. It may be, for example, the automobile field where the polluting waste generated by the motor used to drive the vehicle wheels is desired to be reduced as much as possible.

Still unpublished French patent application FR0109526 assigned to the applicant describes an osmotic actuator intended to be plunged into a biological medium and comprising a deformable enclosure having a semi-permeable membrane, said enclosure containing an osmotically active solute.

SUMMARY OF THE INVENTION

The present invention aims at providing an osmotic actuator and motor that can operate over a long time and the operation of which can be controlled with more accuracy.

More specifically, the present invention provides an actuator intended to be arranged to contact a biological solvent, comprising an enclosure having a wall permeable to the solvent and non-permeable to a first solute and containing microorganisms capable of transforming a second solute into the first solute; and a deformable chamber connected to the enclosure that can see its volume increase under the action of the solvent penetrating into the enclosure by osmosis.

According to an embodiment of the present invention, the enclosure comprises a bundle of hollow fibers colonized by the microorganisms.

According to an embodiment of the present invention, the enclosure has a wall permeable to the second solute.

According to an embodiment of the present invention, the enclosure has a wall non-permeable to the second solute, the microorganisms being capable of transforming a number of particles of the second solute into a higher number of particles of the first solute.

The present invention also provides a motor comprising an actuator such as described hereabove, in which the chamber comprises a return means which opposes to the volume increase of the chamber and a controllable means for decreasing the osmotic pressure in the chamber.

According to an embodiment of the present invention, the motor further comprises a secondary enclosure having a portion permeable to the solvent and non-permeable to the particles of the first and second solutes, and containing microorganisms capable of transforming a number of particles of the second solute into a smaller number of particles of the first solute, said secondary enclosure being connected to the chamber by a valve.

According to an embodiment of the present invention, the enclosure is arranged in a deformable envelope containing the solvent and the first solute, the means for decreasing the osmotic pressure in the chamber being a valve capable of permitting communication between the chamber and the envelope.

According to an embodiment of the present invention, the envelope comprises microorganisms capable of transforming a number of particles of the second solute into a smaller number of particles of the first solute.

According to an embodiment of the present invention, the motor comprises a means for permitting communication between the envelope and a source for supplying substances necessary to the metabolism of the microorganisms.

According to an embodiment of the present invention, the communication means comprises a bundle of hollow fibers crossing the envelope and in which a fluid containing said substances can circulate.

BRIEF DESCRIPTION OF DRAWINGS

The foregoing and other objects, features, and advantages of the present invention will be discussed in detail in the following non-limiting description of specific embodiments in connection with the accompanying drawings, among which:

FIGS. 1A and 1B show two steps of the operation of a first embodiment of a motor according to the present invention;

FIGS. 2A and 2B show two steps of the operation of a variation of the first embodiment of the motor according to the present invention;

FIGS. 3A to 3C show three steps of the operation of a second embodiment of the motor according to the present invention.

DETAILED DESCRIPTION

Figure 4A:
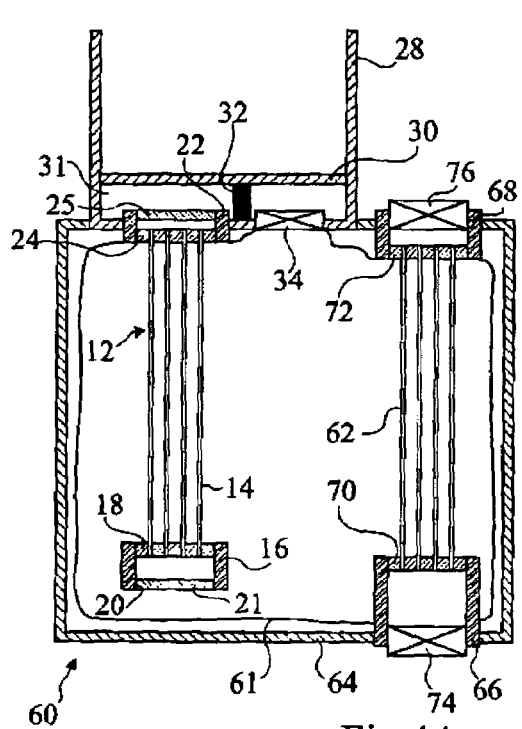
FIGS. 4A to 4D show four steps of the operation of a third embodiment of the motor according to the present invention.

In FIGS. 1A and 1B, an osmotic motor 10 according to the present invention comprises an enclosure 12 formed by a bundle of hollow fibers with a semi-permeable wall 14, for example, of the type used for dialysis operations. The wall of fibers 14 has a cut-off threshold on the order of 200 Daltons, that is, it lets through particles having a molar mass substantially smaller than 200 Daltons, that is, than 200 g/mol. Each fiber has, for example a diameter on the order of 200 µm. Fiber bundle 14 is maintained at a first end by a first junction ring 16, for example, via a gluing area 18. Ring 16 comprises an opening 20 closed by a plug 21. The second end of the fiber bundle 14 is maintained by a second junction ring 22, for example, via a gluing area 24. A membrane 25, having a cut-off threshold on the order of 1000 Daltons, closes second ring 22.

Enclosure 12 is attached at the level of second junction ring 22, to an end of a cylindrical body 28 in which a mobile piston 30 can slide. Mobile piston 30 and the cylindrical body define an expansion chamber 31. A return means 32, for example, a spring, exerts on piston 30 a tensile load tending to bring it back to an idle position. Cylindrical body 28 comprises an outlet valve 34 communicating with the outside of motor 10.

A population of bacterial, vegetal, or animal cells, which are capable of fabricating an osmotically-active substance X is arranged within fibers 14. The cut-off threshold of fibers 14 is set to prevent passing of substance X, while the cut-off threshold of membrane 25 is set to enable passing of substance X, but to block the cells. In the present example, substance X is di-hexose and the cells may consist of *E. Coli* cells genetically engineered to produce the di-hexose. Various genetic engineering means enable having a genetically-engineered cell fabricate di-hexose and export it outside of the cell.

In an initial phase, to arrange the genetically-engineered cells inside of fibers 14, enclosure 12 may be placed alone in an osmotically neutral ambient medium and a culture liquid containing the genetically engineered cells may be slowly circulated inside of fiber bundle 14, via opening 20. The cut-off thresholds of membrane 25 and of the wall of fibers 14 are sufficiently low to retain the cells within fibers 14. The ambient medium comprises a solvent in which are dissolved the nutritive substances essential to the cell metabolism, among which glucose (having a molar mass of approximately 180 Daltons) and oxygen. The cut-off threshold of fibers 14 is determined to let through from the ambient medium to the cells the nutritive substances and to let through, into the ambient medium, the waste generated by the cell metabolism. The genetically-engineered cells can thus colonize the inside of fibers 14. The cells are for example treated to deposit and adhere on the internal wall of fibers 14 in the form of a monolayer. When the colonization has been performed, opening 20 is closed by plug 21.

The cells may further be treated to obtain properties favorizing the long-term operation of the motor. It may be desired to obtain "immortalized" cells to favor the long-term operation of the device. It may also be desired to obtain cells exhibiting a "contact inhibition" to put the entire cell population in a harmonious state enabling, in particular, a good circulation of the nutritive and catabolic substances.

An operating cycle of motor 10 develops as follows.

In normal operation, motor 10 is placed in an ambient medium comprising a solvent in which are dissolved the nutritive substances essential to the cell metabolism, in particular glucose.

FIG. 1A shows motor 10 at the beginning of a cycle. Piston 30 is in its idle position, the volume of expansion chamber 31 being minimum and outlet valve 34 is closed. The genetically-engineered cells produce, from the glucose, di-hexose molecules, which tends to increase the osmotic pressure within fiber bundle 14. The solvent of the ambient medium penetrates into fibers 14 and into expansion chamber 31, thus displacing piston 30. The displacement of piston 30 extends spring 32, enabling storage of mechanical power.

In FIG. 1B, expansion chamber 31 is shown in maximum expansion. Outlet valve 34 then opens. The pressure inside of expansion chamber 31 equalizes with the pressure of the ambient medium. Spring 32 brings piston 30 back to its idle position by evacuating, through outlet valve 34, the solvent from expansion chamber 31 into the ambient medium. The mechanical power stored in spring 32 is then recuperated. Valve 34 is finally closed, thus ending the motor stroke.

Piston 32 may be connected to an external element to which mechanical power is desired to be transmitted.

According to the first embodiment, expansion chamber 31 is formed of a cylindrical body in which a piston slides. According to the desired use of motor 10 according to the present invention, expansion chamber 31 may be formed differently.

FIGS. 2A and 2B show another alternative structure of expansion chamber 31 of motor 10 of the first embodiment. According to this variation, expansion chamber 31 corresponds to the space defined between an inner envelope 36 and an outer envelope 37 as in an air chamber. Inner envelope 36 is deformable and extensible and surrounds a deformable body 38. Outer envelope 37 is flexible and inextensible. It closes back on inner envelope 36 and is connected to junction ring 22 of enclosure 12. Outlet valve 34 is arranged on junction ring 22. As an example, in a medical application of osmotic motor 10 according to the present invention, deformable body 38 may be the human heart and the envelopes may define flange-shaped expansion chambers 31 surrounding the heart.

A cycle of motor 10 according to this variation of the first embodiment is the following.

FIG. 2A shows motor 10 at the beginning of a cycle. The volume of expansion chamber 31 is minimum, deformable body 38 being in maximum expansion, which may correspond to a heart in diastole. Outlet valve 34 is then closed. The genetically-engineered cells generate di-hexose, which causes, by osmosis, the introduction of solvent into expansion chamber 31. Inner envelope 36 deforms and compresses deformable body 38.

In FIG. 2B, deformable body 38 is compressed to a maximum, which may correspond to a heart in systole. On opening of outlet valve 34, the solvent leaves expansion chamber 31, enabling expansion of deformable body 38, which ends the cycle.

According to another variation of the present invention, expansion chamber is formed of a resilient envelope enclosing the fibers which are arranged, for example, in a spiral, the two junction rings being tight. When the cells produce the osmotically-active substance, the fibers tend to straighten and deform the resilient envelope. An outlet valve is provided at the level of a junction ring. At the valve opening, the pressure within the fibers decreases and the envelope tends to recover its initial shape.

According to another variation of the present invention, the enclosure may be connected to the expansion chamber by a flexible duct. This enables advantageously arranging the enclosure in a ambient medium favorable for the solvent and glucose supply, and placing the expansion chamber at a location where mechanical power is desired to be available. In the case of a medical application, the enclosure could be arranged in an adipose tissue, or on the vascular system. In this last case, the fibers may be arranged to form a hollow tube, leaving at its center a cylindrical space enabling circulation of a fluid such as blood. The junction rings may be O-shaped and placed against the wall of a heart vessel. One of the O-shaped junction rings communicates with the expansion chamber by the flexible duct which perforates the blood vessel.

FIGS. 3A to 3C show a second embodiment of an osmotic motor according to the present invention. Motor 40 comprises the components of the motor of the first embodiment and the reference numerals associated therewith are kept.

Motor 40 comprises a first enclosure 12 of the previously-described type and a second enclosure 42. Second enclosure 42 comprises a second fiber bundle 44 maintained at its ends by junction rings 45, 46 by means of gluing areas 47, 48. Second enclosure 42 is attached on cylindrical body 28 at the level of valve 34, by junction ring 45 which comprises a membrane 49 separating expansion chamber 31 from second fibers 44. Second enclosure 42 communicates, at the level of ring 46 via a membrane 52, with a tight deformable vessel 54.

First fiber bundle 14 is colonized by a first population $P_1$ of genetically-engineered cells producing a substance X (for example, lactose) from a substance Y (for example, di-lactose) so that, from an elementary particle of substance Y, more than one elementary particle of substance X is produced. Second fiber bundle 44 is colonized by a second pollution $P_2$ of genetically-engineered cells producing substance Y from substance X so that, to produce an elementary particle of substance Y, more than one elementary particle of substance X is used.

The walls of fiber bundles 14, 44 have a cut-off threshold smaller than the molar mass of substances X and Y. As an example, the cut-off threshold is on the order of 200 Daltons since substance X is lactose and substance Y is di-lactose. Membranes 25, 49, and 52 have cut-off thresholds greater than 1000 Daltons, to let through substances X and Y and maintain the genetically-engineered cells in respective fiber bundles 14, 44.

In normal operation, motor 40 is placed in an ambient medium comprising a solvent in which are dissolved the nutritive substances essential to the cell metabolism, in particular, glucose. The operating cycle of osmotic motor 40 according to the present invention is the following.

FIG. 3A shows motor 40 at the beginning of the cycle. Valve 34 is closed. The concentrations in substance X are identical in vessel 54 and expansion chamber 31, as well the concentrations in substance Y, and in glucose. In first fiber bundle 14, population $P_1$ produces substance X, which increases the osmotic pressure in expansion chamber 31. The solvent of the ambient medium penetrates into first fiber bundle 14, then into expansion chamber 31, thus displacing piston 30 and storing mechanical power by the stretching of spring 32. Meanwhile, in second fiber bundle 44, population $P_2$ produces substance Y, which decreases the osmotic pressure in vessel 54. Vessel 54 sees its volume decrease, without creating effective work since nothing opposes this decrease.

FIG. 3B shows motor 10 at the end of the previously-described step, expansion chamber 31 having a maximum volume.

Valve 34 then opens. The concentrations in substance X and in substance Y balance in fiber bundles 14, 44, expansion chamber 31, and vessel 54. Similarly, the osmotic pressures balance in the different compartments. Piston 30 thus moves under the action of spring 32 down to the position shown in FIG. 3C. Further, vessel 54 expands by filling up with liquid, the work necessary to expand vessel 54 being negligible as compared to that provided by spring 32, the pressures in the ambient medium being low as compared to those present in expansion chamber 31. Valve 34 is then closed, which ends the cycle.

In the second embodiment, the walls of fibers 14, 44 only let through the solvent of the ambient medium as well as the substances involved in the metabolism of the genetically-engineered cells, especially glucose, oxygen, or carbon dioxide.

The second embodiment is particularly advantageous since the exchanges between motor 40 and the ambient medium are reduced with respect to the first embodiment. Indeed, in the first embodiment, the osmotically-active substance, di-hexose, is produced from glucose present in the ambient medium. Further, at the end of a motor cycle, outlet valve 34 is open and most of the di-hexose produced by the cells is released into the ambient medium. In the case of a medical application, the produced di-hexose is released into the human body, which may be a problem. In the second embodiment, there actually is a glucose consumption by the cells, but only for their normal metabolism, that is, in a much smaller proportion than that of the first embodiment.

According to a variation of the second embodiment, substance X may be glucose and substance Y may be lactose. The cut-off threshold of the membranes of fibers 14, 44 then is set to a threshold smaller than that of glucose, for example, 100 Daltons. The glucose necessary to the cell metabolism thus cannot cross these membranes. Vessel 54 then comprises a means for putting it in communication with the ambient medium. It may be, for example, a valve associated with a membrane having a cut-off threshold at 200 Daltons. The valve is for example open for a short time period when the vessel is at a minimum volume. This enables glucose molecules of the ambient medium to penetrate into the vessel. The glucose molecules will enable compensating for the losses linked to the cell metabolism.

FIGS. 4A to 4D show a third embodiment of osmotic motor 60 according to the present invention. Motor 60 comprises the components of motor 10 of the first embodiment and the reference numerals associated therewith are kept.

Enclosure 12 is arranged in a tight deformable envelope 61 which closes back on junction ring 22 and outlet valve 34. The enclosure is filled with a biological liquid. A second bundle of fibers 62 is arranged in envelope 61. Envelope 61 may be arranged in a perforated rigid carter 64 to avoid hindering the deformations of envelope 61. Fiber bundle 62 is maintained at its ends by junction rings 66, 68, for example, by gluing areas 70, 72. Junction rings 66, 68 cross envelope 61 and are attached on rigid carter 64. They each comprise a valve 74, 76 permitting communication between the internal space of fibers 62 and the outside of the carter 64.

First fiber bundle 14 is colonized by a first population $P_1$ of genetically-engineered cells producing a substance X (for example, di-hexose) from a substance Y (for example, quadri-hexose) so that from an elementary Y particle, more than one elementary X particle is produced. A second population P2 of genetically-engineered cells, arranged inside of envelope 61, is capable of producing substance Y from substance X so that, to produce an elementary particle of substance Y, more than one elementary particle of substance X is used. Second population $P_2$ of cells may be deposited on the external walls of fibers 62.

The membranes of fiber bundles 14, 62 have a cut-off threshold greater than the molar mass of glucose but smaller than the molar mass of substances X and Y. As an example, the cut-off threshold is on the order of 200 Daltons when substance X is a di-hexose, and substance Y a quadri-hexose.

Rigid carter 64 may be arranged in a biological medium so that a biological fluid can flow into second fiber bundle 62 when valves 74, 76 are open. Fluid supply and outlet ducts may also be directly connected at the level of junction rings 66, 68. The cut-off threshold, for example, of 100 Daltons, of the membrane of fiber bundle 62 enables passing of the substance necessary to the metabolism of cell populations $P_1$, $P_2$.

An operating cycle of motor 60 according to the third embodiment is the following.

FIG. 4A shows motor 60 at the beginning of a cycle. Valves 34, 74, 76 are closed. Envelope 61 is at its maximum volume. All the compartments contain a solvent where substance X and Y are in solution. First population $P_1$ of cells starts producing substance X, which increases the osmotic pressure in bundle 14 and expansion chamber 31. Second population $P_2$ starts producing substance Y, thus reducing the osmotic pressure inside of envelope 61. The liquid exchanges occur, the liquid flowing towards first fiber bundle 14 and, from there, to expansion chamber 31, causing the displacement of piston 30. The piston is in an ascending phase.

Figure 4B:
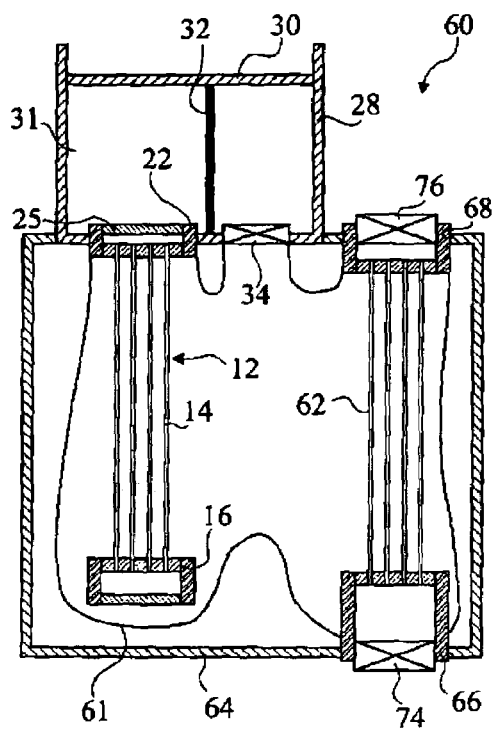

FIG. 4B shows motor 60 at the end of the previously-described step. The concentration in substance Y is minimum in first fiber bundle 14 and maximum inside of envelope 61. Conversely, the concentration in substance X is maximum in first fiber bundle 14 and minimum in envelope 61. The different compartments have a reduced oxygen concentration as compared to the beginning of the cycle and a carbon dioxide concentration greater than that of the beginning of the cycle.

Figure 4C:
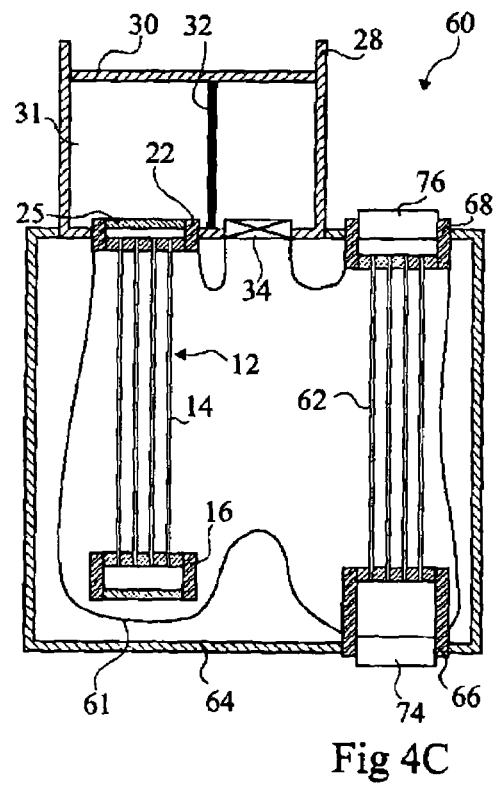

In FIG. 4C, valves 74, 76 are opened to permit communication between second fiber bundle 62 and a fluid external to rigid carter 64. The gas concentrations then balance in all the compartments. Similarly, the glucose concentrations balance between envelope 61 and the external fluid without for the piston position to vary.

Valves 74, 76 are then closed and outlet chamber 34 is opened, which permits direct communication between expansion chamber 31 and envelope 61. The pressure in expansion chamber 31 drops and return spring brings piston 30 back to its initial position evacuating the solvent from expansion chamber 31 to envelope 61. The piston is said to be in a descending phase. First fiber bundle 14 is thus put in communication with the inside of envelope 61. The concentrations in substance X and Y equalize between the two compartments.

Figure 4D:
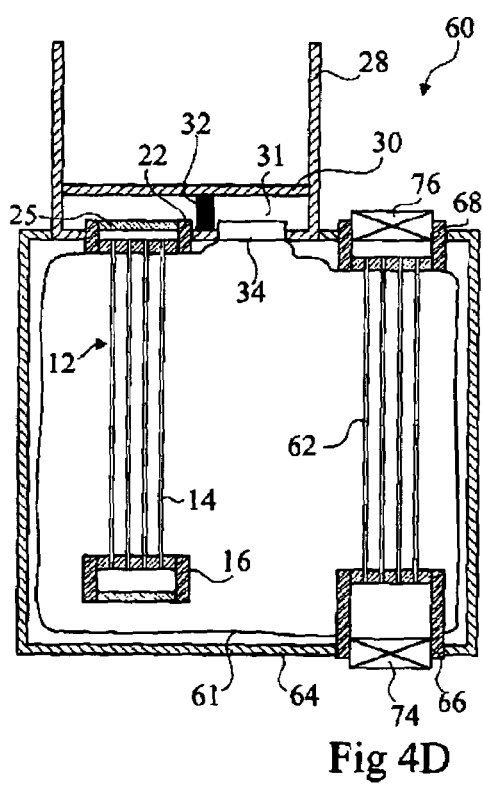

FIG. 4D shows motor 60 at the end of the descending phase of piston 30. Valve 64 is then closed, which ends the cycle.

A variation of the fourth embodiment of the osmotic motor may be used as a motor for driving the wheels of an automobile vehicle. According to this variation, the spring is suppressed and the piston is connected, for example, by a rod to a wheel drive shaft similarly to the connection between a piston of a thermal motor and the crankshaft. The driving power corresponds to the ascending phase of the piston, that is, to the expansion phase of the expansion chamber. In descending phase, when the volume of the expansion chamber decreases, the piston encounters but a small resistance, corresponding to the passing of the solvent through the outlet valve of the expansion chamber. Advantageously, at least two osmotic motors may be arranged in parallel to drive the drive shaft so that the expansion chambers of the motors work in opposition, one being in expansion phase while the other is in contraction phase.

Such a motor may further be used to recover power on braking of the vehicle. In this case, it comprises an additional valve, called the supply valve, arranged between the first fiber bundle and the expansion chamber. Upon operation of the motor to drive the wheels, the supply valve is opened so that the motor operates as described previously.

In the case of a braking, when the piston is in ascending phase, the supply valve is closed and the outlet valve is open so that the expansion chamber fills up with liquid with no significant effort. A large part of the liquid contained in the deformable envelope passes into the expansion chamber without for the concentrations in the various compartments to vary. The supply valve is then opened and the outlet valve is closed. When the piston goes down under the action of the drive shaft driven by the wheels, the liquid contained in the expansion chamber is chased through the fiber bundle and reaches the envelope. The work thus generated enables both slowing down the vehicle and varying the concentrations of substance X and Y. Indeed, the osmolarity of the first fiber bundle increases as the osmolarity in the deformable envelope decreases.

Thereby, when the motor operates again as a wheel drive motor, the supply valve being open, the motor cycle is resumed with a greater efficiency. Indeed, the concentration differences between compartments will create a pressure difference due to which the cycle will be completed faster.

Of course, the present invention is likely to have various alterations, modifications, and improvements which will readily occur to those skilled in the art. In particular, for the second and third embodiments of the motor, the expansion chamber may be formed according to the described variations of the first embodiment.

Further, each enclosure 12, 42, 62 may be formed other than by a fiber bundle. It may have any shape enabling a good exchange of the solutes and of the solvent on either side of the enclosure wall and easing the colonization of the enclosure by a population of genetically-engineered cells.

Moreover, each valve 34, 74, 76 may exhibit any known structure type. The openings and closings of each valve may for example be controlled by a device external to the motor, synchronously or not, or be automatically triggered by the very structure of the valve when the pressure in a compartment of the motor exceeds a determined value.

The invention claimed is:

1. An actuator to be arranged in contact with a biological solvent, comprising:
    an enclosure formed by a wall permeable to the solvent and non-permeable to a first solute, said enclosure containing microorganisms capable of transforming a second solute present in said enclosure into the first solute; and
    a deformable chamber in fluid communication with the enclosure,
wherein, in response to the transformation of the second solute into the first solute by said microorganisms within said enclosure, the solvent penetrates into the enclosure by osmosis and into said deformable chamber, thereby increasing the volume of said deformable chamber.

2. The actuator of claim 1, wherein the enclosure comprises a bundle of hollow fibers colonized by the microorganisms.

3. The actuator of claim 1, wherein said wall of the enclosure is permeable to the second solute.

4. The actuator of claim 1, wherein the wall of the enclosure is non-permeable to the second solute, and
    wherein the microorganisms are capable of transforming a number of particles of the second solute into a higher number of particles of the first solute.

5. A motor comprising an actuator, said actuator comprising:
    an enclosure formed by a wall permeable to the solvent and non-permeable to a first solute, said enclosure containing microorganisms capable of transforming a second solute present in said enclosure into the first solute; and
    a deformable chamber in fluid communication with the enclosure,
wherein, in response to the transformation of the second solute into the first solute by said microorganisms within said enclosure, the solvent penetrates into the enclosure by osmosis and into said deformable chamber, thereby increasing the volume of said deformable chamber, and
wherein the chamber comprises a return means which opposes to the volume increase of the chamber and a controllable means for decreasing the osmotic pressure in the chamber.

6. A motor comprising an actuator, said actuator comprising:
    an enclosure formed by a wall permeable to the solvent and non-permeable to a first solute, said enclosure containing microorganisms capable of transforming a second solute present in said enclosure into the first solute; and
    a deformable chamber in fluid communication with the enclosure,
wherein, in response to the transformation of the second solute into the first solute by said microorganisms within said enclosure, the solvent penetrates into the enclosure by osmosis and into said deformable chamber, thereby increasing the volume of said deformable chamber, said motor further comprising a secondary enclosure having a portion permeable to the solvent and non-permeable to the particles of the first and second solutes, and containing microorganisms capable of transforming a number of particles of the second solute into a smaller number of particles of the first solute, said secondary enclosure being connected to the chamber by a valve.

7. The motor of claim 5, wherein the enclosure is arranged in a deformable envelope containing the solvent and the first solute, the means for decreasing the osmotic pressure in the chamber being a valve capable of permitting communication between the chamber and the envelope.

8. The motor of claim 7, wherein the envelope comprises microorganisms capable of transforming a number of particles of the second solute into a smaller number of particles of the first solute.

9. The motor of claim 8, comprising a means for permitting communication between the envelope and a source for supplying substances necessary to the metabolism of the microorganisms.

10. The motor of claim 9, wherein the communication means comprises a bundle of hollow fibers crossing the envelope and in which a fluid containing said substances can circulate.

11. The motor of claim 6, wherein the enclosure is arranged in a deformable envelope containing the solvent and the first solute, the means for decreasing the osmotic pressure in the chamber being a valve capable of permitting communication between the chamber and the envelope.

12. The motor of claim 11, wherein the envelope comprises microorganisms capable of transforming a number of particles of the second solute into a smaller number of particles of the first solute.

13. The motor of claim 12, comprising a means for permitting communication between the envelope and a source for supplying substances necessary to the metabolism of the microorganisms.

14. The motor of claim 13, wherein the communication means comprises a bundle of hollow fibers crossing the envelope and in which a fluid containing said substances can circulate.

15. The actuator of claim 1, further comprising:
   a junction defining a passage between said enclosure and said deformable chamber; and
   a semi-permeable membrane at said junction and closing said passage.

16. The actuator of claim 15, wherein said membrane is permeable to said first solute and non-permeable to said microorganisms.

17. The motor of claim 5, further comprising:
   a junction defining a passage between said enclosure and said deformable chamber; and
   a semi-permeable membrane at said junction and closing said passage, said membrane being permeable to said first solute and non-permeable to said microorganisms.

18. The motor of claim 6, further comprising:
   a junction defining a passage between said enclosure and said deformable chamber; and
   a semi-permeable membrane at said junction and closing said passage, said membrane being permeable to said first solute and non-permeable to said microorganisms.

* * * * *